(12) United States Patent
Champseix et al.

(10) Patent No.: US 9,243,992 B2
(45) Date of Patent: Jan. 26, 2016

(54) METHOD AND DEVICE FOR FLOW CYTOMETRY WITHOUT SHEATH FLUID (75) Inventors: Henri Champseix, Saint Gely du Fesc (FR); Olivier Magnin, Chapareillan (FR); Bernard Welmant, Montpellier (FR)

(73) Assignee: C2 DIAGNOSTICS, Montpellier (FR)

( * ) Notice: Subject to any disclaimer, the term of this patent is extended or adjusted under 35 U.S.C. 154(b) by 233 days.

(21) Appl. No.: 13/132,574

(22) PCT Filed: Dec. 1, 2009

(86) PCT No.: PCT/FR2009/052349
§ 371 (c)(1),
(2), (4) Date: Jun. 2, 2011

(87) PCT Pub. No.: WO2010/063936
PCT Pub. Date: Jun. 10, 2010

(65) Prior Publication Data
US 2011/0235030 A1 Sep. 29, 2011

(30) Foreign Application Priority Data
Dec. 2, 2008 (FR) ...................... 08 58200

(51) Int. Cl.
*G01N 21/00* (2006.01)
*G01J 1/10* (2006.01)
(Continued)

(52) U.S. Cl.
CPC ............ *G01N 15/1209* (2013.01); *G01N 15/14* (2013.01); *G01N 15/1456* (2013.01); *G01N 33/4915* (2013.01); *G01N 15/1056* (2013.01);
(Continued)

(58) Field of Classification Search
CPC .............. G01N 15/14; G01N 15/1456; G01N 15/1459; G01N 15/1463; G01N 15/1209; G01N 15/1404; G01N 33/4915
See application file for complete search history.

(56) References Cited

U.S. PATENT DOCUMENTS

| 2,656,508 A | 10/1953 | Coulter |
| 3,710,264 A | 1/1973 | Doty et al. |

(Continued)

FOREIGN PATENT DOCUMENTS

| CH | 544305 A | 11/1973 |
| FR | 2653885 | 5/1991 |
| FR | 2873813 A | 2/2006 |

OTHER PUBLICATIONS

Von Behrens W et al: "Comparison of Techniques Improving the Resolution of Standard Coulter Cell Sizing Systems", 1976, Journal of Histochemistry and Cytochemistry, Vol. 24, No. 1, pp. 247-256, XP002535515.

(Continued)

*Primary Examiner* — Gregory J Toatley
*Assistant Examiner* — Hina F Ayub
(74) *Attorney, Agent, or Firm* — Young & Thompson (57) ABSTRACT A method and a device employing the method of flow cytometry, preferably applicable but not limited to the counting and differentiation of leukocytes. It relates more particularly to the field of simplified haematology instruments with moderate operating costs. The method is characterized in that a technique of impedance measurement is used for identifying the particles whose trajectory did not pass through a predetermined optical measurement zone in order to process them selectively, thus avoiding the use of sheath fluids for guiding the particles towards the measurement zone.

17 Claims, 6 Drawing Sheets (51) Int. Cl.
  *G01N 1/10* (2006.01)
  *G01N 15/02* (2006.01)
  *G01N 15/12* (2006.01)
  *G01N 15/14* (2006.01)
  *G01N 33/49* (2006.01)
  *G01N 15/10* (2006.01)
  *G01N 15/00* (2006.01)

(52) U.S. Cl.
  CPC ........ *G01N 15/1227* (2013.01); *G01N 15/1404* (2013.01); *G01N 15/1429* (2013.01); *G01N 15/1459* (2013.01); *G01N 15/1463* (2013.01); *G01N 15/1484* (2013.01); *G01N 2015/008* (2013.01); *G01N 2015/1037* (2013.01)

(56) References Cited

U.S. PATENT DOCUMENTS

| | | | |
|---|---|---|---|
| 4,420,720 A | 12/1983 | Newton et al. | |
| 4,633,169 A | 12/1986 | Degrave et al. | |
| 4,710,021 A * | 12/1987 | von Behrens | 356/72 |
| 4,797,624 A | 1/1989 | Dunstan et al. | |
| 5,335,668 A * | 8/1994 | Nardella | 600/547 |
| 5,719,666 A * | 2/1998 | Fukuda et al. | 356/72 |
| 5,812,419 A | 9/1998 | Chupp et al. | |
| 6,228,652 B1 | 5/2001 | Rodriguez et al. | |
| 6,614,215 B1 | 9/2003 | Wood | |
| 7,916,280 B2 * | 3/2011 | Ueno et al. | 356/39 |
| 2001/0052763 A1 | 12/2001 | North, Jr. | |
| 2002/0028434 A1 * | 3/2002 | Goix et al. | 435/4 |
| 2005/0162648 A1 * | 7/2005 | Auer et al. | 356/318 |
| 2006/0160229 A1 | 7/2006 | Lopez et al. | |
| 2006/0160239 A1 * | 7/2006 | Lee et al. | 436/164 |
| 2006/0263833 A1 * | 11/2006 | Loken et al. | 435/7.23 |
| 2007/0263215 A1 * | 11/2007 | Bachalo et al. | 356/336 |
| 2008/0093216 A1 | 4/2008 | Zhao et al. | |
| 2008/0124745 A1 | 5/2008 | Lefevre | |
| 2008/0286751 A1 * | 11/2008 | Renaud et al. | 435/5 |
| 2009/0033920 A1 * | 2/2009 | Simpson | 356/124 |
| 2009/0117555 A1 * | 5/2009 | Kuypers et al. | 435/6 |
| 2009/0190121 A1 * | 7/2009 | Hegyi et al. | 356/28 |
| 2011/0205535 A1 * | 8/2011 | Soller et al. | 356/300 |

OTHER PUBLICATIONS

French Search Report, dated Jul. 6, 2009, in FR 0858200.
International Search Report, dated Mar. 24, 2010, in PCT/FR2009/052349.

* cited by examiner

V. Kachel, Flow cytometry and Sorting, Wiley-Liss Inc., 1990

Prior Art

Figure 11

METHOD AND DEVICE FOR FLOW CYTOMETRY WITHOUT SHEATH FLUID

TECHNICAL FIELD

The present invention relates to the field of automatic devices for the counting and characterization of particles suspended in a liquid medium, and more particularly the field of haematology instruments for counting and characterizing the various types of cells contained in a blood sample.

It relates in particular but is not limited to a method for counting and classifying leukocytes.

The present invention also relates to a device employing said method.

PRIOR ART

Normal leukocytes are classified in five types: monocytes, lymphocytes, neutrophils, eosinophils and basophils. The total number of leukocytes and their relative distribution in these five subpopulations makes it possible to establish or to guide the practitioner towards a pathology.

The state of the art and the proposed invention thus relate to devices for counting the number of leukocytes contained in a blood sample and for determining their relative distribution among the five subpopulations.

The known document U.S. Pat. No. 2,656,508 of W. H. Coulter et al. describes a method for absolute counting of particles in suspension by impedance measurement. According to this method, the number of particles per unit volume is determined by a technique of impedance measurement which consists of measuring the change in impedance of a micro-orifice when a blood cell passes through it. This technique, which is simple and robust, does not require complex fluidic devices and is freely usable since U.S. Pat. No. 2,656,508 which protected it dates from 1953. It is therefore regularly used by all manufacturers of automatic devices (Beckman Coulter, Abbott, Bayer, C2 Diagnostics, Sysmex, ABX, etc.) for absolute counting of the number of leukocytes.

It is known that in this technique of impedance measurement, the shape of a pulse generated by the passage of a cell depends on the geometry of the micro-orifice and on the trajectory of the cell in the latter. There is, for example, the article by Von Behrens et al. (Von Behrens, J. of Histochemistry and Cytochemistry, 1976, Vol. 24, No. 1, p. 247), which describes the geometry of the lines of the electric field generated in an orifice of rectangular or circular section, and the shape of the resistive pulses as a function of the trajectory of the cell or particle in said orifice. Most of the devices of the prior art try to minimize this dependence of the shape of the resistive pulse on the trajectory by optimizing either the geometry of the orifice, as described for example by T. Zhao et al. in document US 2008/0093216, or the arrangement and structure of the electrodes, as described for example in documents U.S. Pat. No. 4,420,720 of Newton et al. and US 2001/0052763 of North et al., respectively.

However, the technique of impedance measurement does not, on its own, provide reliable differentiation of the five subpopulations of leukocytes. This differentiation of the leukocytes according to their five subpopulations is advantageously carried out by combining impedance measurement with optical flow cytometry techniques. The known document U.S. Pat. No. 5,812,419 of V. L. Chupps et al. describes a method of automatic analysis of blood cells that combines, as well as impedance measurement, optical measurements of absorption, spectrophotometry, diffraction at different angles and fluorescence. According to this method, the measurements by impedance measurement and optical flow cytometry are performed in different analysis cells, and data-merging algorithms enable the desired cell counting and characterization to be obtained. The method described by Chupps et al. clearly shows the benefit of the combined use of impedance measurement and optical flow cytometry, but the use of different analysis cells makes the system very complex. Moreover, possible inhomogeneity of the blood samples analysed by the different methods is an appreciable source of measurement uncertainty.

In document U.S. Pat. No. 6,228,652 C. M. Rodriguez et al. describe a cytometry cell for performing measurements of impedance and optical measurements simultaneously on the same cells, thus achieving simplification of the device and reduction of the problems of correlating measurements between multiple transducers. The device according to U.S. Pat. No. 6,228,652 thus makes it possible to measure, for each cell, its volume, which is a function of its resistivity with direct voltage, its radio-frequency opacity which is a function of its conductivity at the electrical frequency of measurement, and its optical characteristics of diffraction and fluorescence.

Simplification of devices is a considerable industrial challenge in the development of automatic devices for haematology, as it opens up considerable markets in small health care facilities and in the emerging countries. For example, document FR 2 653 885 of D. Lefevre et al. describes a device for optical and electrical cytometry in which the electrodes for resistivity measurement are constituent parts of the device for transfer of the flow of cells.

Optical flow cytometry imposes important constraints in terms of relative positioning of the flow containing the cells and the means of illumination. In fact, it is important for the quality of the optical measurements for the cells to pass through the beam in a zone, called the optical measurement zone, where the illumination can be regarded as sufficiently uniform in intensity. A cell passing through the beam in a zone where the illumination is incorrect can give rise to an incorrect measurement and an error in determination of the type of cell. The difficulty therefore consists of forcing the flow transporting the cells to circulate in such a way that it is entirely inside the optical measurement zone of uniform intensity.

The solution generally employed in the devices of the prior art includes the use of one or more sheath flows, also called sheath streams, which circulate concentrically with the central stream transporting the cells. These sheath flows draw out the central stream, and thus very accurately confine the particles that it contains. Thus, FR 2 653 885 for example employs a technique of double sheathing, according to which the central stream is confined by two concentric sheath flows. Generation of the sheath flow and of the central stream transporting the blood cells requires multiple fluidic inlets as well as micro-nozzles. This leads to particularly dense assemblies of fluidic components around the measurement zone, making assembly of the sensors difficult and expensive. Moreover, for the localization of the particles by the sheath flow to be effective, the flow rate of the sheath flow must be much greater than the flow rate of the flow containing the sample. This means that a considerable volume of the reagent employed, generally a diluent, is of no chemical use but is merely used for guiding the sample flow to be measured. The effects in terms of consumption of reagents and production of waste are obvious.

Moreover, the degree of dilution used in solutions of this type is incompatible with the degree of dilution required for the measurement of haemoglobin, which is generally measured with dilution of the leukocytes and therefore makes additional dilution necessary, as well as additional expensive fluidic elements.

The purpose of the present invention is to propose a method of flow cytometry comprising measurements of impedance and optical measurements, which does not require a sheathing flow, thus permitting considerable simplification of the measurement cell and of the associated fluidic elements.

Another purpose of the present invention is to propose a device employing the method, which is simpler and more economical both to manufacture and to maintain, than the devices of the prior art, so that automatic devices thus equipped can be used by smaller laboratories while preserving an equivalent quality of measurement.

DISCLOSURE OF THE INVENTION

This objective is attained with a method of flow cytometry for particle characterization comprising steps of:
- transfer of a fluid containing particles through an aperture flow-cell, said aperture flow-cell being at least in part substantially transparent to at least one wavelength of interest, and at least in part substantially insulating to electricity,
- measurement of the electrical impedance variation generated by the passage of said particles contained in the fluid through the aperture flow-cell,
- measurement of at least one optical property of said particles, which interact with at least one light beam passing through the aperture flow-cell,
- characterization of said particles by using said measurements of electrical impedance variation and optical properties, characterized in that it further comprises steps of:
- deducing information on the trajectory of the particles in the aperture flow-cell, at least from the analysis of said measurement of the electrical impedance variation,
- exploitation of said information on the trajectory for conditioning the characterization of the particles.

According to particularly advantageous characteristics,
- the method according to the invention is a flow cytometry method that does not require the use of a sheath flow or sheathing flow as in the methods of the prior art. The principle of the physical confinement of the particles by the sheath fluids is replaced by the possibility of carrying out selective processing of the data obtained from the measurements on the particles, said processing being conditioned or determined by information on their trajectory;
- only the fluid containing the particles is passed through the aperture flow-cell;
- the aperture flow-cell can be simplified considerably in comparison with the devices of the prior art. It can be reduced to a simple aperture or orifice in the wall of a cell, through which the fluid containing the particles is conveyed and in which the measurements are carried out.

Advantageously,
- the measurement of the electrical impedance variation can comprise a measurement of resistivity carried out in direct current;
- the measurement of the electrical impedance variation can also comprise at least one complex impedance measurement carried out at at least one non-zero frequency;
- the at least one optical property measured can be one of the following optical properties: absorbance, elastic scattering at at least one angle, inelastic scattering at at least one angle, elastic backscattering, inelastic backscattering, autofluorescence, fluorescence at at least one wavelength caused by at least one marker attached to the particles, fluorescence at at least one wavelength caused by at least one marker attached to at least one element contained in the particles, polarization of light;
- the particle characterization can comprise a classification of the particles;
- the particle characterization can also comprise a counting of the particles;
- the analysis of the electrical impedance variation can comprise a comparison between the measured electrical impedance variation and at least one element of comparison among at least one model of electrical impedance variation and at least one previously defined numerical value, the result of said comparison determining whether the trajectory of the particles has traversed a previously defined zone of the aperture flow-cell;
- the data relating to the particles whose trajectory did not pass through a previously defined zone of the aperture flow-cell can be removed from the data used for the classification of said particles. Thus, it is possible in the method according to the invention to sort the particles in relation to their trajectory, for example so as only to keep the data from those that meet certain conditions;
- the measured optical property of the particles can also be compared with at least one element of comparison among at least one model of optical property and at least one previously defined numerical value. In this case, if the results of the comparisons of the electrical impedance variation and of the optical property with their models or respective previously defined numerical values do not satisfy at least one previously defined criterion, the data relating to the particles can be removed from the data used for the classification of said particles;
- the operation of classification of the particles can comprise steps of attribution to the particles of a set of values or coordinates obtained from the analysis of said measurements carried out during their passage through the aperture flow-cell, said coordinates defining their position in a previously defined representation space, and steps of segmentation of said representation space into distinct regions, said regions grouping together particles with substantially similar characteristics;
- the particles can comprise blood cells. These blood cells can be leukocytes.

According to another aspect of the invention, a flow cytometry device is proposed for particle characterization comprising:
- an aperture flow-cell at least in part substantially transparent to at least one wavelength of interest, and at least in part substantially insulating to electricity,
- means for transfer of a fluid containing particles through said aperture flow-cell,
- means for measurement of the electrical impedance variation generated by the passage of said particles contained in the fluid through the aperture flow-cell,
- means for measurement of at least one optical property of the particles, said particles interacting with at least one light beam passing through the aperture flow-cell,
- means for analysis of said measurements of variation in electrical impedance and of optical properties, characterized in that it comprises:
- means for deducing information on the trajectory of the particles in the aperture flow-cell, at least from the analysis of said measurement of the change in electrical impedance, and means for exploitation of said information on the trajectory for conditioning the characterization of the particles.

The device according to the invention can further comprise means for preparation of the particles of interest before their transfer through the aperture flow-cell. The particles of interest are the particles that we wish to analyse and classify, and which it may be necessary to separate from other particles present in the sample, notably by methods of lysis or of dilution in the case of blood cells.

Advantageously,

- the geometry of the aperture flow-cell can be adapted in such a way that the measured electrical impedance variation during passage of the particles depends substantially on their trajectory in said aperture flow-cell. This result can be obtained for example with an aperture flow-cell of substantially rectangular section whose longitudinal edges end in corners with low radius of curvature. It should be noted that here we are looking for a result opposite to the practice in the devices of the prior art, in which it is rather expected to minimize this dependence on the trajectory of the particles;
- the aperture flow-cell can comprise an internal cross-section substantially of one of the following forms: circular, rectangular;
- the aperture flow-cell can be constituted of at least one of the following materials: sapphire, ruby, glass, plastic;
- the means for measurement of the electrical impedance variation generated by the passage of the particles can comprise at least two electrodes arranged respectively on either side of the orifice of the aperture flow-cell, said electrodes being in electrical contact with the fluid containing the particles;
- the means for measurement of the electrical impedance variation generated by the passage of the particles can also comprise at least one electrode arranged in the orifice of the aperture flow-cell, said electrode being in electrical contact with the fluid containing the particles. A device according to the invention can thus comprise for example electrodes distributed along the wall of the aperture flow-cell. At least one of the electrodes can also be a constituent element of the means for transfer of the fluid containing the particles;
- the means for measurement of the optical property of the particles can comprise at least one light source, and at least one means of optoelectronic detection;
- the means for measurement of the optical property of the particles can also comprise at least one optical means of focusing light coming from the light source in the aperture flow-cell;
- the means for measurement of the optical property of the particles can also comprise at least one optical means of collecting the light originating from the aperture flow-cell;
- the means for measurement of the optical property of the particles can further comprise at least one means for spectral filtering of the light coming from the particles to be characterized;
- at least one of said optical means of measurement of the optical property of the particles can be integrated in the aperture flow-cell. Said integration is for example possible by using an aperture flow-cell moulded in plastic, whose external walls would constitute lenses for focusing and optionally for collecting the light. Optical elements such as an optoelectronic detector for example can also be glued directly on the aperture flow-cell.

According to a particular embodiment, the means for optoelectronic detection can be arranged in such a way as to measure a light beam coming from the particles to be characterized that has an angular orientation different from that of the axis of the beam originating from the light source. Such a configuration makes it possible, for example, to do scattering measurements at non-zero angles.

According to another particular embodiment, the means for measurement of the optical property of the particles can comprise a light source having a known state of polarization, and means for optoelectronic detection comprising means for analysis of the polarization of the light.

According to yet another aspect of the invention, an instrument for blood analysis is proposed comprising at least one device according to the invention, the particles to be analysed being blood cells, and notably leukocytes.

DESCRIPTION OF THE FIGURES AND EMBODIMENTS

Other advantages and features of the invention will become apparent on reading the detailed description of applications and embodiments, which are in no way limitative, and the following attached drawings:

FIG. 2a represents a case when the flow of the particles is not centred in the beam, whereas in FIG. 2b the flow of particles is centred in the beam. The effect is illustrated for the case, which is in no way limitative, of measurements of absorbances;

FIG. 5a shows examples of trajectories of particles inside an aperture flow-cell of cylindrical shape, as well as the delimitation of the reliable optical measurement zone as defined in FIG. 3. FIG. 5b shows the shape of the resistive pulses that would be obtained for particles travelling along the trajectories shown in FIG. 5a;

FIG. 9a shows a case when all the particles detected are represented. FIG. 9b only shows the particles sorted in accordance with the method of the invention;

An embodiment that is preferred, but is not in any way limiting, of the device employing the method according to the invention in an instrument for counting and characterizing the various types of cells contained in a blood sample, and in particular leukocytes, will be described, referring to the drawings. This instrument can be used, for example, for determining the total number of leukocytes and their relative distribution in their five subpopulations: monocytes, lymphocytes, neutrophils, eosinophils and basophils.

In the rest of the description, the particles are assumed to be white blood cells or leukocytes, but this is not intended to be limiting in any way.

Figure 1:
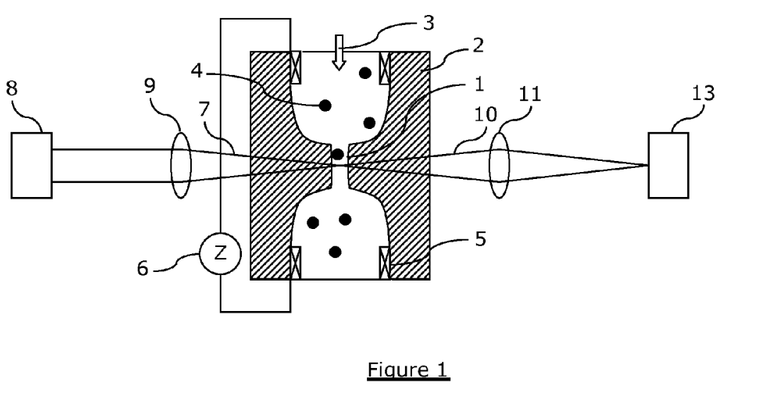
FIG. 1 shows a schematic diagram of the device according to the invention.

Referring to FIG. 1, the device employing the method according to the invention comprises an aperture flow-cell 2, through which a fluid 3 containing particles 4 is passed. This aperture flow-cell comprises an orifice 1, where the interactions between the particles and the means of measurement mainly occur. Transfer of the fluid 3 through the aperture flow-cell 2 can be done by various techniques while remaining within the scope of the invention, among which we may notably mention flow by gravity, aspiration, and injection under pressure.

Preferably, aperture flow-cell 2 and orifice 1 are of substantially circular cross-section, and orifice 1 has a diameter of the order of 80 μm. These specifications are not, of course, in any way limiting, and a device according to the invention can also just as well comprise an aperture flow-cell 2 of substantially rectangular section, or polygonal, with a different size.

To allow impedance measurements and optical measurements, the aperture flow-cell 2 must be constituted at least in part of at least one material that is substantially insulating to electricity, and at least in part of at least one material that is substantially transparent at the optical wavelengths of interest. According to a preferred embodiment, it is made of sapphire. It is of course possible, while remaining within the scope of the invention, to employ an aperture flow-cell 2 made of some other material, such as ruby, a glass, a polymer or a plastic, or even made with a combination of several materials.

According to a preferred embodiment, electrodes 5 are arranged on either side of the aperture flow-cell 2. They are in electrical contact with the fluid, so as to enable a longitudinal electric field to be established in the aperture flow-cell and in particular through orifice 1. These electrodes 5 are connected to a device 6 which measures the impedance variations during passage of the particles 4 through the orifice 1 of the aperture flow-cell 2, i.e. the temporal shape and the amplitude of the pulses due to passage of these particles. The measurement of impedance employed in the device according to the invention is preferably, but is not limited to, a measurement of resistivity carried out with direct current.

According to a preferred embodiment, the device according to the invention comprises at least one device for optical measurements, the general principle of which is measurement of the result of an interaction between a particle such as a leukocyte and a light beam. Said measurement is also called measurement of an optical property of the particle.

Referring to FIG. 1, such a device for optical measurement can notably comprise a light source 8, and at least one detecting means 13. It can also comprise at least one optical means for focusing 9 the beam 7 in the aperture flow-cell 2, and at least one optical means for collecting 11 the light from the aperture flow-cell 2.

The light source 8 can for example be a laser, a laser diode, or a light-emitting diode.

The optical means for focusing 9 and for collecting 11 can notably comprise spherical, aspherical, or cylindrical lenses, or freeform optics, with gradient of indices and/or reflecting surfaces (mirrors). They can also comprise at least one light guide, which for example guides the beams originating from the measurement zone towards the sensitive surface of the detecting means 13.

The detecting means 13 can comprise at least one photodetector such as a photodiode, an avalanche photodiode or a photomultiplier tube.

Advantageously, at least one of the optical means for focusing 9 and for collecting 11 can be at least in part integrated with the aperture flow-cell 2, for example by bonding or by adapting the external shape of the latter so as to constitute the surface of a lens. It is also possible to fix the detecting means 13 directly on the aperture flow-cell 2, optionally without employing collecting means 11.

According to an embodiment that is preferred, but is not in any way limiting, of the device according to the invention, a measurement of absorbance is employed, in which a variation of light intensity is measured on the detector 13 when a leukocyte traverses the light beam 7. So this is the measurement of this optical property which will be developed in the rest of the description. However, a person skilled in the art will easily be able to use the method according to the invention in devices employing measurement of other optical properties of the particle, while remaining within the scope of the invention.

Advantageously, according to this embodiment,
the light source 8 can be a light-emitting diode emitting in the blue;
the optical device for focusing 9 can be constituted of an adjustable plane-parallel plate allowing beam 7 to be centred on the aperture flow-cell 2, and an achromatic doublet and a cylindrical lens for focusing the beam 7 in the aperture flow-cell 2, which in the preferred embodiment is substantially cylindrical;
the optical device for collecting 11 can be constituted of two plano-convex lenses imaging the zone of interaction of the light with the particles 4 on the detecting means 13, comprising for example a photodiode.

Figure 2:
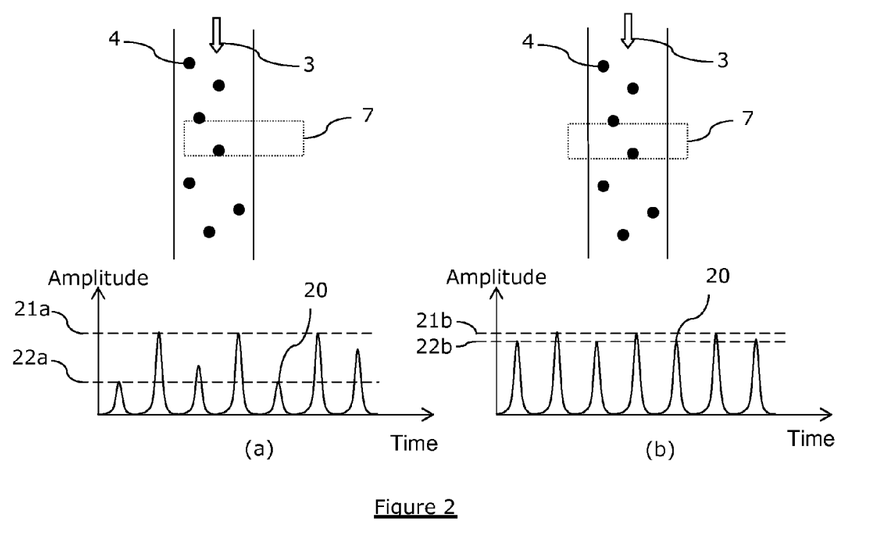
FIG. 2 illustrates the influence of the positioning of the particles in the light beam in flow cytometry.

To obtain reliable results, it is necessary for the optical measurement zone, where the interactions occur between the particles and the light, to have limited dimensions, for example of the order of 100 μm×30 μm, and for the intensity distribution of the incident light to be substantially homogeneous there. The difficulty consists of constraining the flow transporting the particles to be circulated so that it passes entirely inside said optical measurement zone. This problem is illustrated in FIG. 2 for the non-limitative case of measurements of absorbance on particles having substantially identical absorbance. When all of the flow 3 of particles 4 traverses the optical measurement zone 7, the absorbance peaks 20 all have substantially the same amplitude, between 21b and 22b. If the flow 3 transporting the particles reaches or even exceeds the limit of the optical measurement zone 7, as shown in FIG. 2a, the particles 4 no longer receive an equal amount of light and the optical measurement is faulty. The error is characterized by considerable variability, between 21a and 22a, of the amplitude of peaks 20, which is in its turn reflected in increased uncertainty in classification of the particles.

Figure 3:
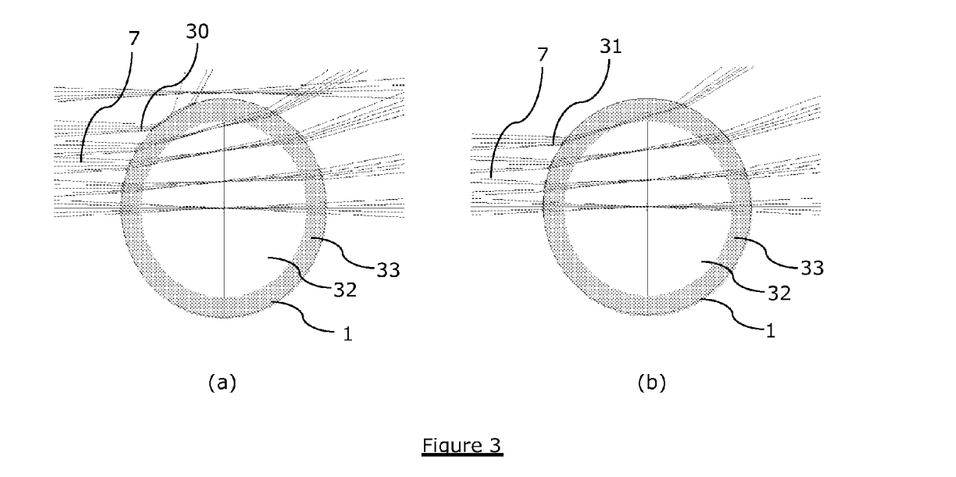
FIGS. 3a and 3b illustrate the deflection of a light beam by the surface of a cylindrical orifice, and the resultant delimitation of the zones of reliable optical measurements.

FIG. 3 illustrates the deflection of a light beam 7 by the surface of a cylindrical orifice such as the orifice 1 of the aperture flow-cell 2. In FIG. 3a, the beam is larger than the diameter of the orifice 1. Owing to the angle of incidence on the inside surface of orifice 1, certain portions 30 of this beam 7 are reflected or at least strongly refracted and in consequence a peripheral zone 33 of orifice 1 is not illuminated sufficiently uniformly. In FIG. 3b, the beam is smaller than the diameter of the orifice 1. Similarly, a peripheral zone 33 of orifice 1 located beyond the limiting ray 31 is not illuminated correctly. In both cases, only the particles that passed through the so-called reliable optical measurement zone 32 will be measured in proper conditions. Those that pass through zone 33 can give faulty results. This reasoning can of course easily be extended by a person skilled in the art to other geometries of orifices 1 and of aperture flow-cells 2 while remaining within the scope of the invention.

Figure 11:
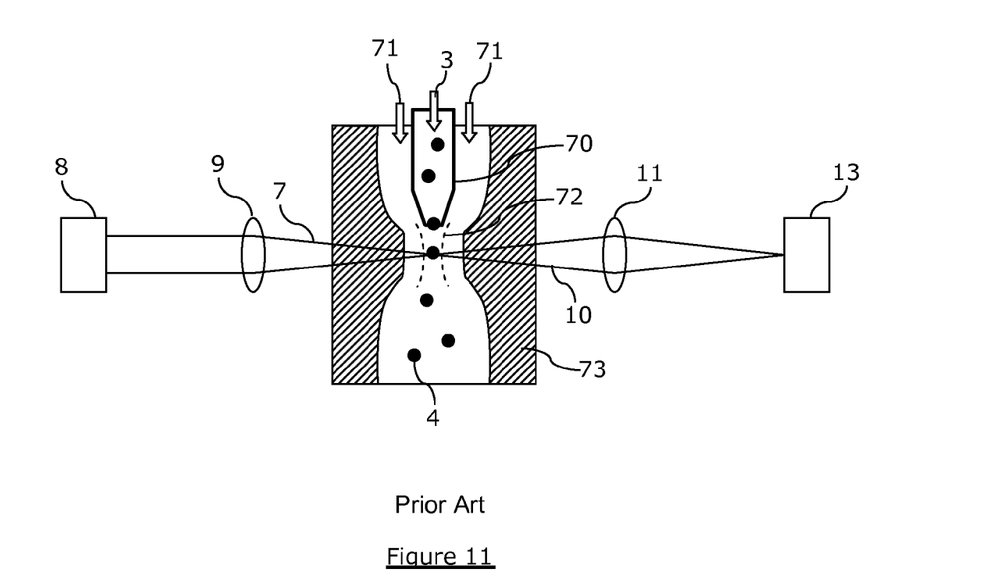
FIG. 11 shows a schematic diagram of a device of the prior art employing confinement of the particles in the optical measurement zone by means of sheath fluids.

The solution generally adopted in the devices of the prior art, as shown in FIG. 11, comprises confinement 72 of the flow 3 transporting the particles 4 to the centre of the measurement cell 73, by means of one or more concentric sheath flows 71, with all the drawbacks already mentioned in terms of complexity, manufacturing cost and operating cost, notably owing to the use of injectors 70.

The solution adopted in the method according to the invention comprises, in contrast, identification of the particles whose trajectory in the aperture flow-cell does not pass through a predetermined zone, for example the reliable optical measurement zone 32, so that they can be treated differently when the data are analysed. This identification can notably be carried out by analysing the shape of the pulses obtained from the impedance measurement. In other words, the information on the trajectory of the particles 4 in the orifice 1 of aperture flow-cell 2 deduced notably from analysis of the changes in electrical impedance is exploited for influencing the operation of characterization of the particles, i.e. for modifying the manner in which the measurements are used.

Figure 4:
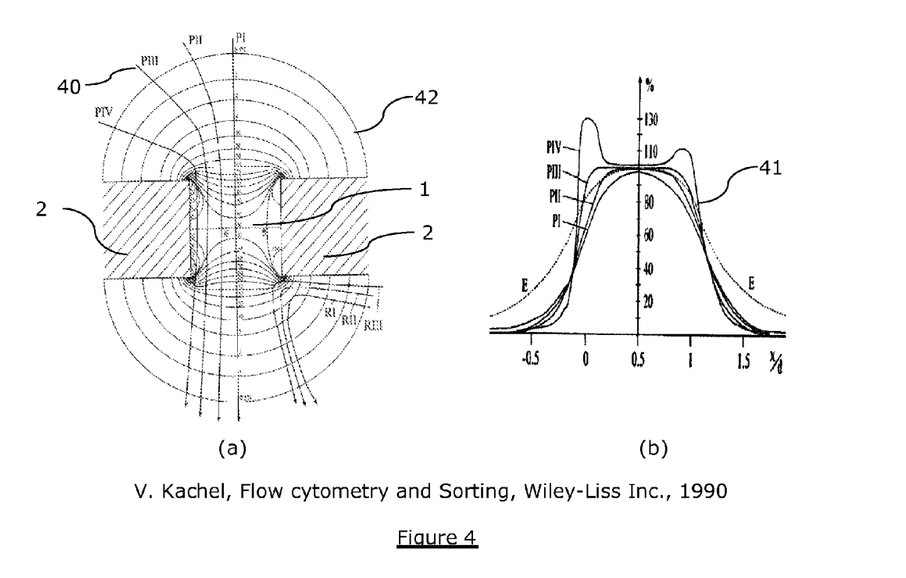
FIG. 4a presents an example of the form of equipotential lines appearing in a microscopic opening made in an insulating material, when a voltage is applied through said opening.
FIG. 4b illustrates the shape of the resistive pulses obtained when particles pass through this opening, according to various trajectories. These illustrations are taken from V. Kachel, Flow cytometry and Sorting, Wiley-Liss Inc., 1990, also cited in US 2008/0093216.

Referring to FIG. 4, when a particle such as a leukocyte traverses an opening in which an electric field is applied, the temporal change in resistivity across said opening, which can be the orifice 1 of the aperture flow-cell 2 of the device according to the invention, takes the form of a pulse 41, the shape of which largely depends on the trajectory 40 of the particle. In particular, it can be seen in the example in FIG. 4 that said pulse 41 becomes broader and finally has a plateau and then rebounds, as the trajectory of the particle moves farther away from the centre of the aperture flow-cell 2. This effect is due to the shape of the electric field, whose equipotential lines 42 around and in the opening 1 are illustrated in FIG. 4a.

This effect, which is regarded in the devices of the prior art as a source of error that has to be minimized, is exploited advantageously in the present invention. It makes it possible to characterize the trajectories of particles in the aperture flow-cell based on analysis of the shape of the resistive pulses, and said shape can be regarded as a signature of these trajectories.

The arrangement and the surface of the electrodes 5 on either side of the cell 2 as well as the geometry of said cell 2 can even be advantageously designed so that the shape of pulse 41 is strongly dependent on the trajectory of the particle, which goes against the concepts employed in the devices of the prior art. However, an orifice 1 of cylindrical shape ending in corners with a low radius of curvature, as employed in a preferred embodiment, already displays the required characteristics.

Figure 5:
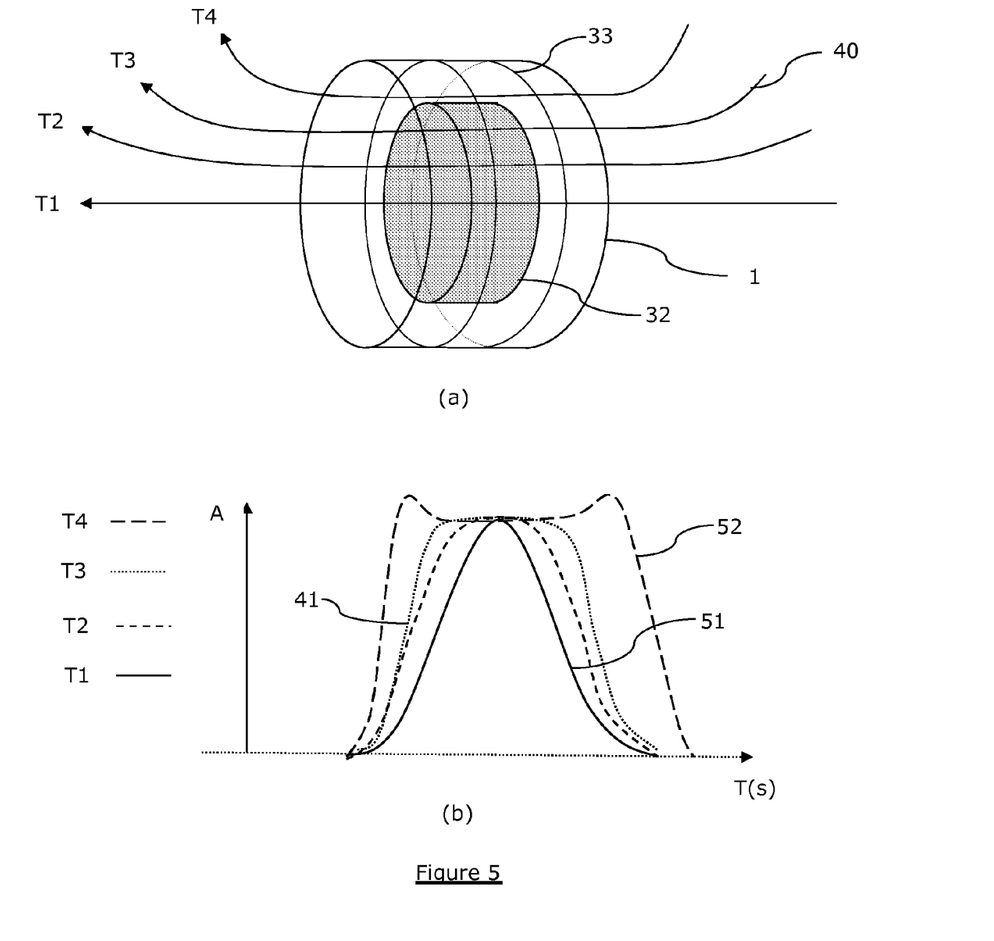

An example of signatures representative of trajectories of particles in an aperture flow-cell is shown in FIG. 5. In this example the optical measurement zone is in the form of a cylinder that corresponds to the interior of the orifice 1 of aperture flow-cell 2, which can also be of roughly cylindrical shape. The reliable optical measurement zone 32 is represented by a circumscribed cylinder in the total optical measurement zone, and the signature of the optimum trajectories T1 of particles passing through said reliable optical measurement zone 32 is approximately Gaussian 51. This signature has a plateau that becomes wider as the trajectory moves farther away from the centre of the orifice (trajectories T2, T3, T4). It is therefore possible to associate, at the limit of the reliable optical measurement zone 32, a pulse shape or a limiting signature and determine, relative to a mathematical criterion, whether a trajectory is valid (signature 51) or invalid (signature 52). The change in the shape of the resistive pulses such as shown in FIG. 5 is of course a non-imitative example, as their behaviour can differ according to the geometry of the aperture flow-cell and according to the type of particles.

According to the preferred embodiment, the mathematical criterion applied for determining the validity of a trajectory results from comparison of the pulses measured with at least one limit value of pulse width for at least one height of said pulse.

According to a preferred but non-limitative embodiment employing a measurement of resistivity and a measurement of optical absorbance, the particles passing through the aperture flow-cell therefore generate two pulses, or electrical signals: a resistive pulse originating from the impedance measurement sensor and a pulse originating from the optical absorbance sensor.

The optical pulses are conditioned analogically, amplified and filtered according to the usual techniques in order to be transmitted to the analogue/digital converter.

The resistive pulses are obtained by conventional techniques but particular care is taken in application of the sensor in order to maximize the signal-noise ratio and obtain sufficient information for characterization and sorting, such as the choice of the bandwidth.

These signals obtained from the impedance measurement and optical absorbance sensors are conditioned and transmitted to an analogue/digital converter, which is connected to a digital processing system, which can notably include a microprocessor and/or an FPGA and/or a DSP. The sampling rate of the optical and resistive pulses is adapted to each type of signal so as to obtain the amount of information necessary for digital processing.

The processing of the optical pulses can be limited to extraction of the information on amplitude and width.

The sampled signal originating from the resistive sensor is shaped by conventional signal processing techniques based on the time and frequency characteristics of the signal to be analysed such as digital filtering with finite or infinite pulse response, optimal filtering, fast Fourier transform etc.

We can thus create a pair, formed from the resistive pulse and the associated optical pulse, and store their characteristics, for example the amplitudes, pulse widths, etc.

The resistive and optical pulses, cleaned of the background noise and normalized, can then be processed by the sorting algorithm, which classifies the measurements in at least two categories, called valid and invalid.

Figure 7:
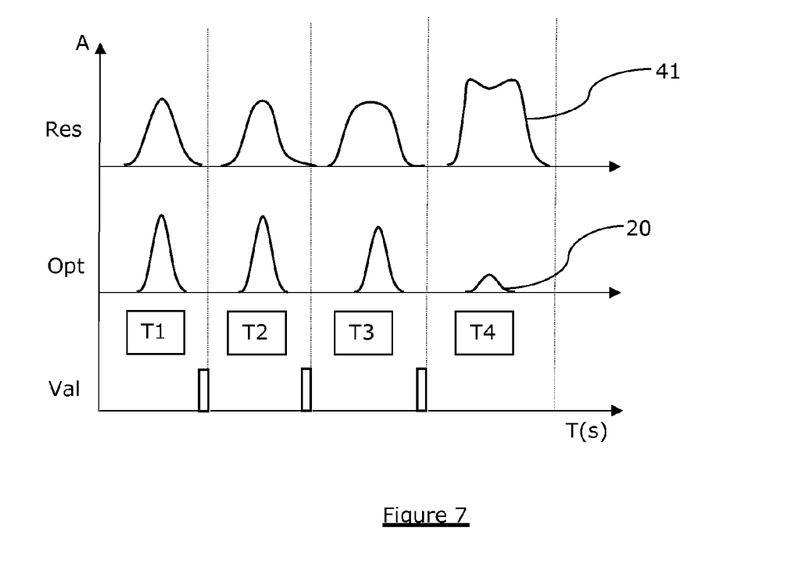
FIG. 7 shows a timing diagram of the data acquisition and processing in accordance with the flow chart in FIG. 6.
Figure 8:
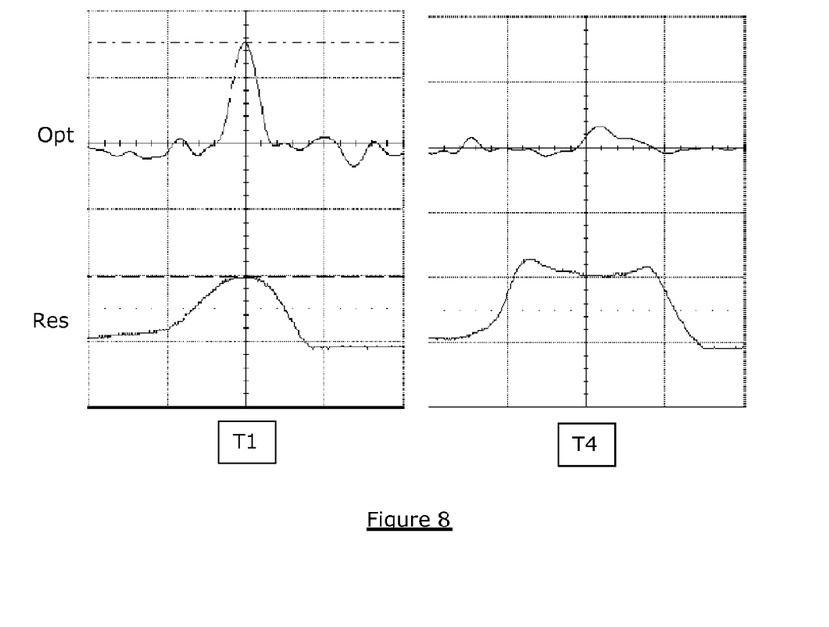
FIG. 8 shows examples of measured signals corresponding respectively to resistive pulses and to optical pulses resulting from measurements of absorbance. These signals are representative, respectively, of trajectories T1 and T4 as shown in FIG. 5.

Advantageously, the sorting algorithm comprises a measurement of the difference between a signature associated with an optimum trajectory, represented by an optimum resistive pulse shape, and the signature of the effective trajectories of the particles, i.e. of the measured resistive pulses. If this difference is too large, the data relating to these particles are regarded as invalid. FIG. 8 shows examples of the result of measurement of valid and invalid resistive (Res) and optical (Opt) pulse pairs. They correspond respectively to measurements relating to particles that followed trajectories such as T1 and T4 in FIG. 5. The timing diagram in FIG. 7 illustrates the time sequence of the acquisition and classification (Val) of the measurements.

Figure 6:
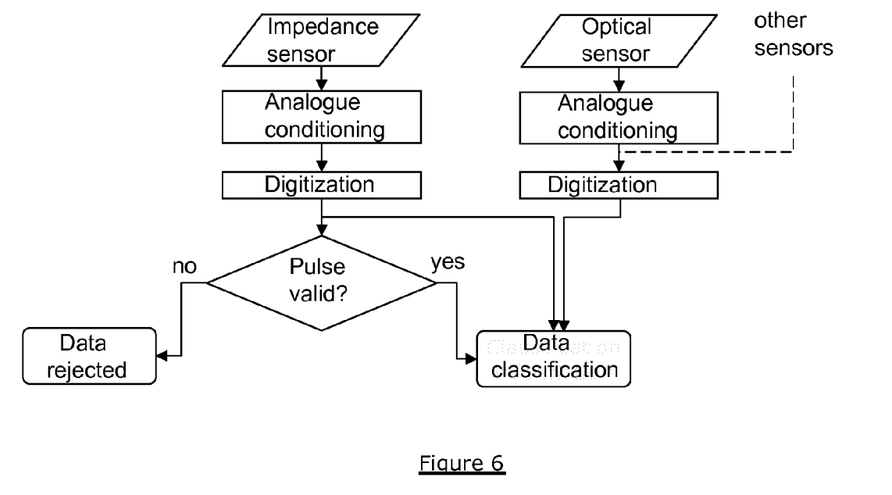
FIG. 6 shows a flow chart of the data acquisition and processing according to a preferred embodiment of the method according to the invention.

The characterizing algorithm, which performs the actual analysis of the results, advantageously comprises at least one operation of classification of the particles in categories having substantially uniform characteristics, and optionally at least one operation of counting of said particles. According to an embodiment that is advantageous but does not in any way limit the method, the classification only uses data relating to the particles whose pulses or signatures have been classified as valid, as illustrated in the flow chart in FIG. 6. Conversely, the count can be performed on all the measurements that gave rise to a resistive pulse, whether valid or invalid. Any other manner of exploitation of the data after sorting of the particles can of course be envisaged, while remaining within the scope of the invention.

Figure 9:
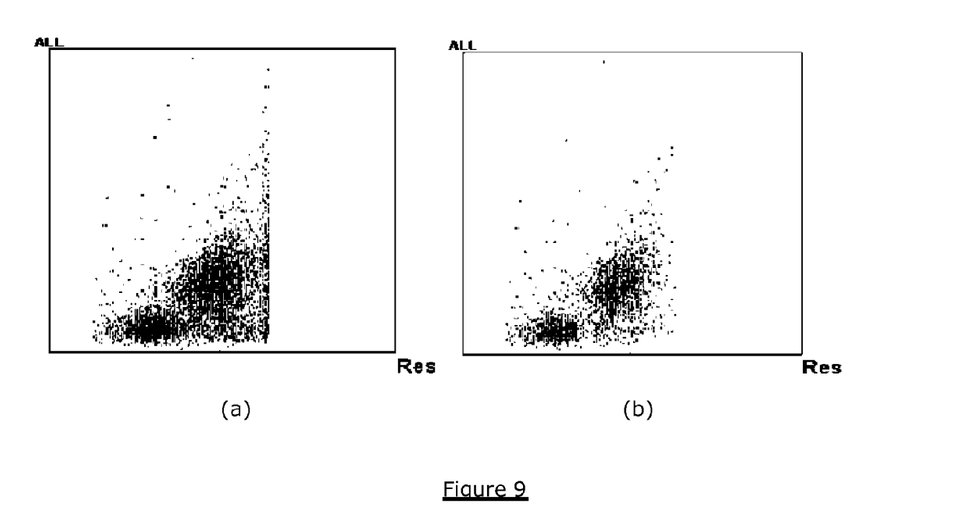
FIG. 9 shows examples of diagrams of classification of particles, in this case leukocytes, obtained with a device according to the invention.

The classification of valid particles, or according to a preferred embodiment, of leukocytes in subcategories, can advantageously be carried out by attributing to said particles a set of values or coordinates originating from analysis of the resistive and optical measurements carried out during their passage through the aperture flow-cell 2, said coordinates defining their position in a previously defined representation space. Segmentation of this representation space into separate regions grouping together particles of substantially similar characteristics then makes it possible to identify the population of each of the subcategories, for example for measuring their relative size. FIG. 9 shows an example of representation of the particles, in this case leukocytes, as a function of the data obtained respectively from analysis of the resistive measurements (Res) and measurements of optical absorbance (ALL). Each point represents a pair of measurements. FIG. 9a shows all the measurements, valid and invalid. FIG. 9b only shows the valid measurements, which makes it possible to reveal separate groups of points corresponding to different categories of particles.

Figure 10:
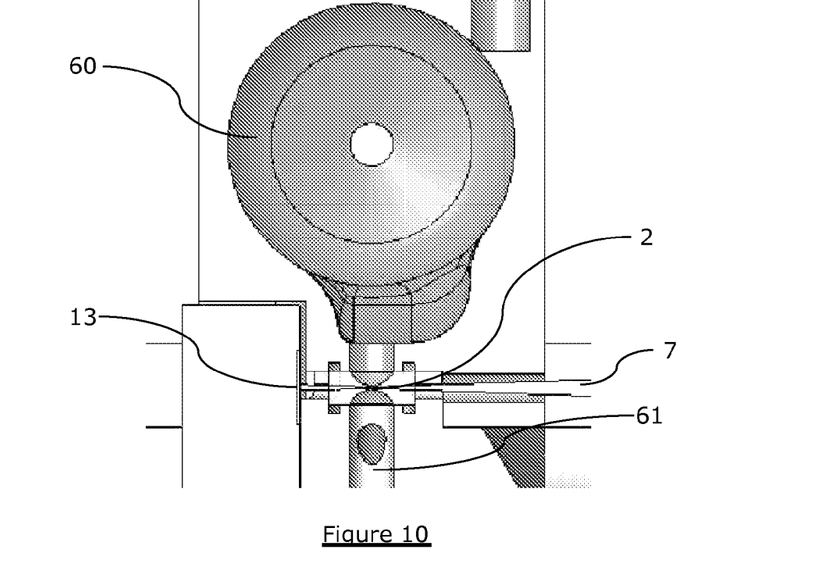
FIG. 10 shows an embodiment, which is preferred but is not in any way limiting, of a device according to the invention.

According to an advantageous characteristic of the invention, the method and the device can easily be applied for making a particularly simple haematology instrument. The device according to the invention can easily be mounted on a simple vessel 60 containing the solution to be analysed, and its associated orifice 61. The aperture flow-cell 2 can be mounted in any position relative to the vessel. Said aperture flow-cell can also be mounted in a continuous pipeline and can be made of any type of material that is substantially transparent and is an electrical insulator. Transfer of the solution to be analysed can for example be effected by aspiration through the aperture flow-cell 2. FIG. 10 shows a non-limitative example of application, comprising a single optical measurement in the axis of the orifice. Several photodiodes can also be placed around the axis of the orifice to permit measurements at various angles and various wavelengths.

Advantageously this embodiment also makes it easy to combine a conventional measurement of haemoglobin by spectrophotometry through the translucent vessel containing the solution to be analysed.

According to particular embodiments, the device according to the invention can comprise a plurality of electrodes distributed in one or more layers along the aperture flow-cell 2, as described in document U.S. Pat. No. 4,420,720 for example. The device according to the invention can also comprise electrodes of variable or non-variable resistivity, covering all or part of the inside surface of the aperture flow-cell 2, as described in US 2001/0052763 for example. In the case of a device according to the invention comprising more than two electrodes, it is possible to use several measurements of impedance between different pairs of electrodes.

According to particular embodiments it is possible, while remaining within the scope of the invention, to use complex impedance measurements at one or more discrete frequencies, as well as in one or more continuous electrical frequency bands.

According to particular embodiments, it is possible to use, while remaining within the scope of the invention, at least one measurement of at least one optical property such as for example:

- a measurement of autofluorescence, a measurement of fluorescence caused by a marker attached to the leukocyte membrane, or a measurement of fluorescence caused by a marker attached to one or more elements of the intracellular contents of the leukocytes, in which a luminous intensity is measured at a fluorescence wavelength on at least one detector 13 arranged around the aperture flow-cell, said detector being for example isolated from the light at the excitation wavelength 7 by a spectral filter;
- a measurement of elastic scattering at at least one angle, of inelastic scattering at at least one angle, of backscattering, for which notably one or more detectors 13 can be arranged around the aperture flow-cell, at orientations different from that of the axis of the beam 7, so as to measure the light scattered at different angles, which may have shifts in optical frequency;
- a measurement of polarization, in which the detecting means 13 are designed so as to analyse the polarization of the light that has interacted with the particle, the source 8 having a known, for example linear, polarization.

According to particular embodiments it is possible, in a device according to the invention, to use the measurements of several optical properties simultaneously, for example by arranging several devices for optical measurement as shown in FIG. 1 at different orientations or according to different axes around the aperture flow-cell 2, or by introducing means for splitting the beam 10 originating from the aperture flow-cell.

According to particular embodiments, the mathematical criterion applied for determining the validity of a trajectory can result from:

- at least one comparison with a threshold in amplitude, or a minimum pulse height,
- at least one calculation of distance in the mathematical sense between a measured pulse and at least one pulse model, said distance being calculated for example by means of a normalized correlation function,
- at least one analysis carried out on the result of application of at least one transformation such as a Fourier transform to the measured pulses,
- or any combination of these methods or any other appropriate mathematical method, while remaining within the scope of the invention.

According to particular embodiments it is also possible, while remaining within the scope of the invention, to define one or more models of optical pulses, to compare the optical pulses measured with said model or models and to include this comparison in the sorting algorithm. In addition, it is possible to define one or more paired models of optical and resistive pulses and carry out operations of comparison and sorting based on these models. This can make it possible to process other cases of measurement errors, due for example to particles that do not belong to the expected categories, or to the fact that several particles are measured at the same time.

According to particular embodiments, the method and the associated device can be employed in a device made on the basis of technologies relating to the field of microsystems (MEMs), or of optical microsystems (MOEMs), for example so as to integrate all of the fluidic, electrical and optical functions in a single component.

According to other particular embodiments, the method and the associated device can be employed for the measurement of particles other than biological cells, for example ceramic particles within the context of the manufacture of industrial powders, or pigments within the context of paint manufacture.

Of course, the invention is not limited to the examples that have just been described, and numerous adjustments can be made to these examples without exceeding the scope of the invention.

The invention claimed is:

1. Method of flow cytometry without sheath fluids for particle characterization, comprising steps of:
    transfer of a fluid (3) containing particles (4) through an orifice (1) of an aperture flow-cell (2), said aperture flow-cell being at least in part substantially transparent to at least one wavelength of interest, and at least in part substantially insulating to electricity,
    measurement of electrical impedance variation of the particles generated by the passage of said particles (4) contained in the fluid (3) through the orifice (1) of the aperture flow-cell (2) using electrodes (5) arranged on opposite sides of said aperture flow-cell (2) so as to establish a longitudinal electric field through said orifice (1) and to obtain electrical impedance variation of the particles in a form of pulses (41) the shape of which depend on a trajectory of the particles (4) within said orifice (1) due to non-uniform geometry of the lines of said electric field,
    measurement of at least one optical property of said particles (4), which interact with at least one light beam (7) passing through the orifice (1) of the aperture flow-cell (2),
    characterization of said particles (4) by using said measurements of electrical impedance variation of the particles and optical properties of the particles,
    deducing information on the trajectory of the particles (4) within the orifice (1) of the aperture flow-cell (2), at least from the analysis of the shape of the pulses (41) of said measurement of electrical impedance variation,
    use of said information on said trajectory at least for the exploitation of said measurements of optical properties during said characterization of the particles, comprising a rejection of the measurements corresponding to particles (4) whose trajectory is outside a pre-defined reliable optical measurement zone (32) associated with a limiting signature in the shape of the pulse (41),
    wherein only the fluid (3) containing particles (4) is passed through the aperture flow-cell (2).

2. Method according to claim 1, characterized in that the measurement of the electrical impedance variation comprises a measurement of resistivity carried out with direct current and/or at least one complex impedance measurement carried out at at least one non-zero frequency.

3. Method according to claim 1, characterized in that the at least one optical property measured is one of the following optical properties: absorbance, elastic scattering at at least one angle, inelastic scattering at at least one angle, elastic backscattering, inelastic backscattering, autofluorescence, fluorescence at at least one wavelength caused by at least one marker attached to the particles, fluorescence at at least one wavelength caused by at least one marker attached to at least one element contained in the particles, polarization of light.

4. Method according to claim 1, wherein the particle characterization comprises a classification of the particles (4) into a plurality of subpopulations, including a number of particles in each subpopulation.

5. Method according to claim 4, characterized in that the particle characterization comprises a counting of the particles (4).

6. Method according to claim 4, characterized in that the analysis of the electrical impedance variation comprises a comparison between the measured electrical impedance variation and at least one element of comparison among at least one model of electrical impedance variation and at least one previously defined numerical value, the result of said comparison determining whether the trajectory of the particles (4) has traversed the pre-defined reliable optical measurement zone (32) of the aperture flow-cell (2).

7. Method according to claim 6, characterized in that the data relating to the particles (4) whose trajectory did not pass through the pre-defined reliable optical measurement zone (32) of the aperture flow-cell (2) is removed from the data used for the classification of said particles (4).

8. Method according to claim 6, characterized in that
    the measured optical property of the particles (4) is compared with at least one element of comparison among at least one model of optical property and at least one previously defined numerical value,
    if the results of the comparisons of the electrical impedance variation and of the optical property with their respective models or previously defined numerical values do not satisfy at least one previously defined criterion, the data relating to the particles (4) is removed from the data used for the classification of said particles (4).

9. Method according to claim 4, characterized in that the operation of classification of the particles (4) comprises steps of:
    attribution to the particles of a set of values or coordinates obtained from the analysis of the measurements carried out during their passage through the aperture flow-cell (2), said coordinates defining their position in a previously defined representation space,
    segmentation of said representation space into distinct regions, said regions grouping together particles of substantially similar characteristics.

10. Method according to claim 1, characterized in that the particles (4) comprise blood cells.

11. Method according to claim 1, characterized in that the measurement of the electrical impedance variation comprises a measurement of resistivity carried out with direct current and/or at least one complex impedance measurement carried out at at least one non-zero frequency.

12. Method according to claim 1, wherein the particles (4) comprise blood cells and the characterization is determining a total number of leukocytes and relative distribution in each of five subpopulations comprising monocytes, lymphocytes, neutrophils, eosinophils and basophils, including a respective number of particles in each subpopulation.

13. A method of flow cytometry without sheath fluid for leukocytes characterization, comprising the steps of:
    transferring a blood sample (3) containing leukocytes leukocytes (4) through an orifice (1) of an aperture flow-cell (2), said aperture flow-cell being transparent to at least one wavelength of interest and insulating to electricity,
    wherein electrodes (5) are arranged on opposite sides of said aperture flow-cell (2), the electrodes establishing a longitudinal electric field through said orifice (1), and wherein only the blood sample (3) containing leukocytes (4) is passed through the aperture flow-cell (2);

measuring an electrical impedance variation of the leukocytes when passing through the orifice (1) and through the longitudinal electric field extending through said orifice (1), in order to obtain an electrical impedance variation of the leukocytes represented as resistance pulses (41) having a shape that depends on a trajectory of the leukocytes (4) within said orifice (1) due to non-uniform geometry of the lines of said longitudinal electric field;

using an optical sensor that detects a light beam (7) passing through a pre-defined reliable optical measurement zone (32) of the orifice (1), measuring an optical property of said leukocytes (4) traversing and interacting with the light beam within the pre-defined reliable optical measurement zone (32) and rejecting measurements corresponding to leukocytes (4) having trajectories outside the pre-defined reliable optical measurement zone (32) so as to obtain a filtered set of trajectories, wherein within the pre-defined reliable optical measurement zone (32) an intensity distribution of incident light is homogeneous and the rejection is associated with a limiting signature in the shape of the pulses (41) so that data relating to the leukocytes (4) whose trajectory did not pass through the pre-defined reliable optical measurement zone (32) is removed from the filtered set of trajectories; and using both said resistance pulses and corresponding ones of said optical pulses of said filtered set of trajectories, as paired data, characterizing said leukocytes to determine a total number of leukocytes and a relative distribution in each of plural subpopulations.

14. Method according to claim 13, wherein the analysis of the electrical impedance variation comprises a comparison between the measured electrical impedance variation and at least one element of comparison among a model of electrical impedance variation and a previously defined numerical value, the result of said comparison determining whether the trajectory of the leukocytes (4) has traversed the pre-defined reliable optical measurement zone (32) of the aperture flow-cell (2).

15. Method according to claim 14, wherein the pre-defined reliable optical measurement zone (32) has a size of 100 µm×30 µm.

16. Method according to claim 14, wherein the pre-defined reliable optical measurement zone (32) has a size of 100 µm×30 µm.

17. Method according to claim 13, wherein the plural subpopulations comprise each of monocytes, lymphocytes, neutrophils, eosinophils and basophils.

* * * * *